United States Patent [19]

Hori

[11] Patent Number: 5,697,891
[45] Date of Patent: Dec. 16, 1997

[54] SURGICAL RETRACTOR WITH ACCESSORY SUPPORT

[75] Inventor: Koichiro Hori, Framingham, Mass.

[73] Assignee: Vista Medical Technologies, Inc., Carlsbad, Calif.

[21] Appl. No.: 778,974

[22] Filed: Jan. 6, 1997

[51] Int. Cl.$^6$ .................................................. A61B 17/02
[52] U.S. Cl. .................................... 600/245; 600/201
[58] Field of Search .................................. 600/201, 227, 600/235, 205, 219, 223, 245

[56] References Cited

U.S. PATENT DOCUMENTS

| | | | |
|---|---|---|---|
| 1,036,497 | 8/1912 | Krebs | 600/245 X |
| 1,706,500 | 3/1929 | Smith | 600/245 X |
| 4,627,421 | 12/1986 | Symbas et al. | 600/245 X |

FOREIGN PATENT DOCUMENTS

| | | | |
|---|---|---|---|
| 432042 | 11/1911 | France | 600/245 |
| 168216 | 9/1921 | United Kingdom | 600/245 |

*Primary Examiner*—Jeffrey A. Smith
*Attorney, Agent, or Firm*—Pandiscio & Pandiscio

[57] ABSTRACT

A surgical retractor assembly includes an elongated base bar, a first leg extending from the base bar and substantially normal thereto, a first gripper disposed on the first leg, a second leg mounted at a proximal end thereof on the base bar and extending parallel to the first leg, the second leg proximal end being coupled to and movable along the base bar, and a second rib gripper disposed on the second leg. A U-shaped flexible rail is mounted proximate first and second ends thereof, respectively, on the first and second legs, with a bend portion of the rail extending proximate the base bar. An accessory support member is mounted on the rail and is slidably movable thereon, the accessory support member being adapted to retain an accessory device such that an operative end of the accessory device is disposed generally between the first and second legs.

17 Claims, 2 Drawing Sheets

5,697,891

SURGICAL RETRACTOR WITH ACCESSORY SUPPORT

BACKGROUND OF THE INVENTION

1. Field of the Invention

The invention relates to retractors and is directed more particularly to an assembly including, in combination, a retractor means and an accessory support means.

2. Description of the Prior Art

The use of retractors in cardiothoracic surgery is well known. In keeping with the movement toward minimally invasive surgery, procedures for heart surgery have moved from splitting the breast bone to making a relatively small incision between a pair of ribs which are spread apart by a retractor. An example of such a retractor is shown in FIG. 1 and described hereinbelow.

The use of television (TV) cameras in surgery is also generally well known, it being now commonplace to place a TV camera in or over a surgical site and to have a display within view of the surgeon. However, in heart surgery the mounting of a TV camera above the surgical site usually makes it difficult for the surgeon to see the point of interest as the surgeon's head and hands often obscure the camera's view of the surgical site.

Accordingly, there is a need for a means for mounting a TV camera, or other accessory device, in the close vicinity of an exposed heart in such manner that the camera readily and easily may be moved while the lens of the camera remains directed at the surgical site.

SUMMARY OF THE INVENTION

An object of the invention is, then, to provide a retractor and a camera support assembly, the camera support assembly serving to retain a camera at the surgical site, and to render movement of the camera substantially effortless, while substantially maintaining the camera lens directed at the surgical site.

A further object of the invention is to provide an assembly including, in combination, a retractor and a camera, or other accessory device, wherein the retractor may be a selected one of retractors currently available.

A still further and more general object of the invention is to provide, in combination, a spreader tool and accessory support structure, such that an accessory device mounted on the accessory support structure may be of assistance in conducting work between items spread by the spreader tool.

With the above and other objects in view, as will hereinafter appear, a feature of the present invention is the provision of a surgical retractor assembly. The assembly includes an elongated base bar, a first leg extending from the base bar and substantially normal thereto, a first gripper disposed on the first leg, a second leg mounted at a proximal end thereof on the base bar and extending substantially parallel to the first leg, the second leg proximal end being movable along the base bar, and a second gripper disposed on the second leg. The assembly further includes a U-shaped flexible rail fixed proximate a first end thereof on the first leg and movably mounted proximate a second end thereof on the second leg, with a bend portion of the rail extending proximate the base bar. An accessory support member is mounted on the rail and is slidably movable thereon, the accessory support member being adapted to retain an accessory device such that an operative end of the accessory device is disposed generally between the first and second legs.

In accordance with a further feature of the invention, there is provided a surgical spreader assembly assembly including an elongated base bar, a first leg extending from the base bar and substantially normal thereto, a first gripper disposed on the first leg, a second leg mounted at a proximal end thereof on the base bar and extending parallel to the first leg, the second leg proximal end being movable along the base bar, and a second gripper disposed on the second leg. The assembly further includes a U-shaped flexible rail fixed proximate a first end thereof on the first leg, and movably mounted proximate a second end thereof on the second leg, with a bend portion of the rail extending proximate the base bar. An accessory support member is mounted on the rail and is slidably movable thereon, the accessory support member being adapted to retain an accessory device such that an operative end of the accessory device is disposed generally between the first and second legs.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

In the drawings, like numerals refer to like parts.

DESCRIPTION OF THE PREFERRED EMBODIMENT

Figure 1:
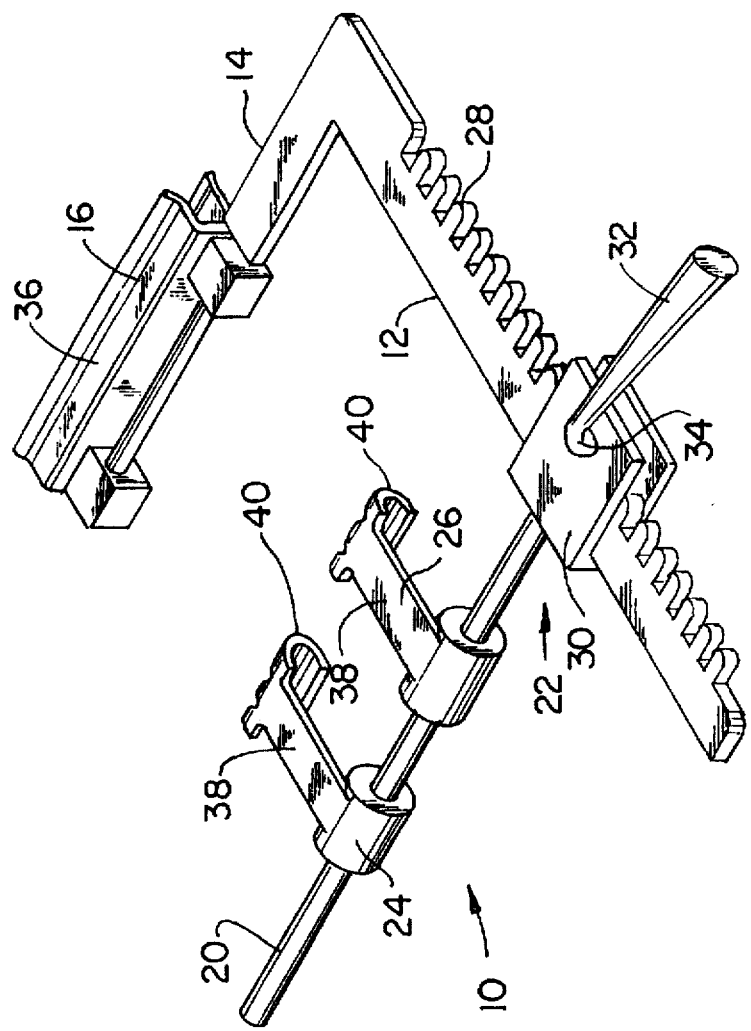
FIG. 1 is a perspective view of a prior art retractor.

Referring to FIG. 1, it will be seen that a prior art retractor 10 includes an elongated base bar 12 and a first leg 14 that extends from and is substantially normal to base bar 12. Leg 14 is fixed to or may be formed integrally with base bar 12. A first gripper 16 is mounted on first leg 14.

A second leg 20 has a proximal end 22 that is attached to a carriage 30 that is mounted for movement on and longitudinally of base bar 12. Leg 20 extends substantially parallel to first leg 14. A second gripper 24 and, if desired, one or more additional grippers 26, is mounted on second leg 20.

As shown in FIG. 1, base bar 12 is provided with a rack of teeth 28. The carriage 30 is engaged with and movable along base bar 12. A handle 32 is rotatably mounted on carriage 30. The inner rotatable end 34 of the handle is attached to a rotary gear (not shown) that engages rack teeth 28, the connection (not shown) between handle 32 and the aforesaid rotary gear (not shown) is such that rotation of the handle about its rotational axis will cause carriage 30 to move in one direction or an opposite direction along base bar 12, according to the direction of rotation of handle 32., so as to move second leg 20 toward or away from first leg 14.

In the known retractor illustrated in FIG. 1, the first gripper 16 comprises a channel member 36 and each of the grippers 24, 26 includes an arm 38 having curved fingers 40 at its free end. Grippers 16, 24, and 26 are sized and shaped so as to be able to engage and retract ribs or other human or animal bone or tissue.

Figure 2:
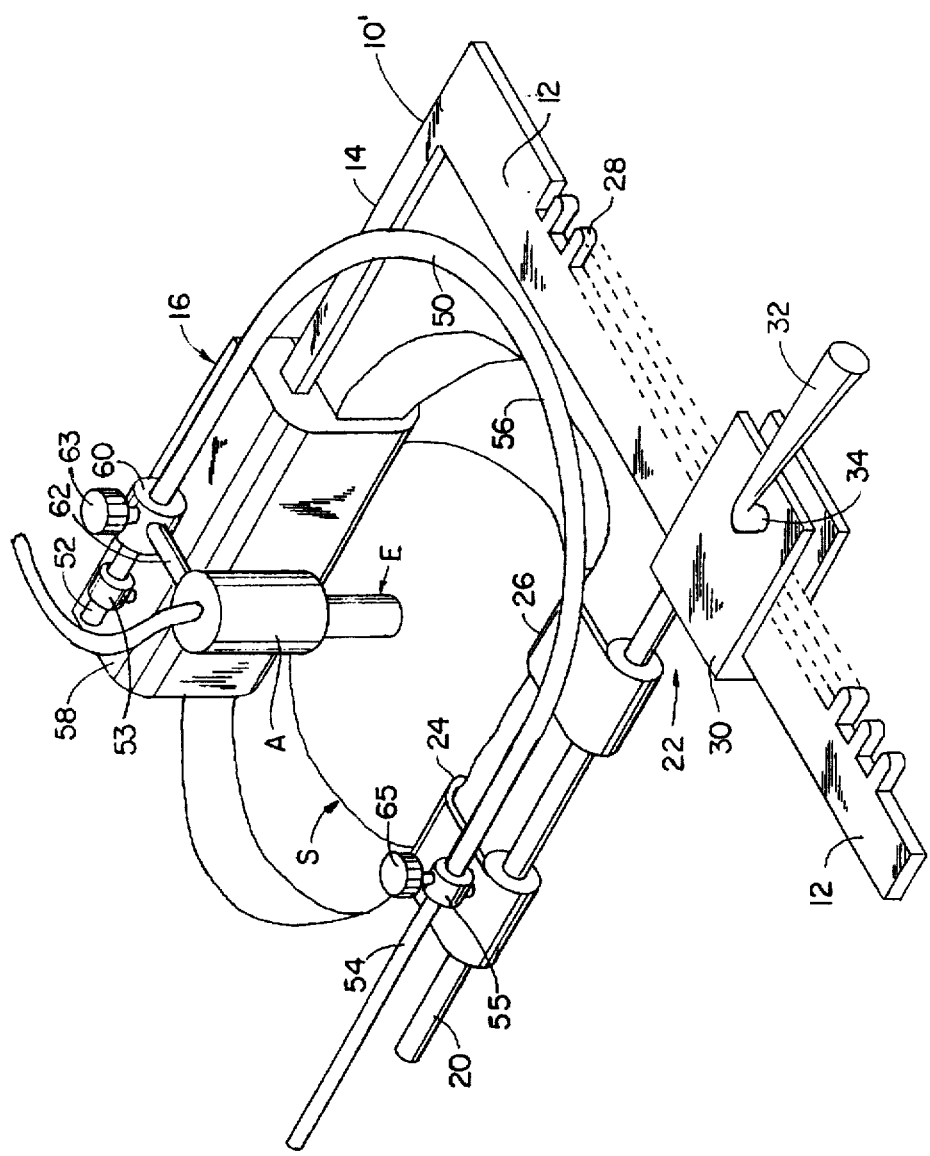
FIG. 2 is a perspective view of one form of surgical retractor assembly illustrative of an embodiment of the invention.

Referring to FIG. 2, it will be seen that an illustrative embodiment of the invention includes, in combination with a retractor 10' of the type described hereinabove, a U-shaped flexible spring-like rail 50 having first and second opposite ends 52 and 54 that are received in two sleeves 53 and 55 respectively. In this preferred embodiment sleeve 53 is fixed to a modified gripper 16' that is carried by the first leg 14, while sleeve 55 is fixed to gripper 24. Gripper 16' may be fixed to leg 14 or may be sized and shaped so as to be slidable thereon toward and away from base bar 12.

Rail 50 may be made of a metal alloy or other material and comprises a bent or arcuate portion 56 that extends toward, and is in part proximate to, the base bar 12. Rail 50 is movable relative to sleeves 53 and 55. Preferably rail 50 has a circular cross-section. Rail 50 also is sufficiently resilient to allow its ends 52 and 54 to move toward or away from one another in accordance with corresponding movement of leg 20 relative to leg 14. The degree of stiffness of rail 50 is such as to accommodate but not prevent relative movement of leg 20 relative to leg 14. Preferably sleeve 55 is provided with a tapped hole that receives a thumb-style lock screw 65 that can be screwed down into tight engagement with rail 50, thereby locking the rail against movement relative to that sleeve and gripper 14. The other sleeve 53 may but need not have a like lock screw arrangement.

An accessory support member 60 is slidably disposed on rail 50 and is manually movable on the rail between a position adjacent first leg 14 and gripper 16' (as shown in FIG. 2) to a position adjacent second leg 20, that is, along an approximately 180° sweep. Support member 60 has a hole of circular cross-section sized to make a close fit with rail 50 while allowing it to slide or rotate retlative to the rail. The accessory support member 60 includes a support arm 62 to which is connected an accessory A, which preferably is a TV camera, but may be a light source or other helpful accessory for the task at hand. The operative end E of the accessory, that is, the lens portion of a camera, or the light emitting portion of a light source, is disposed between first and second legs 14, 20 and is directed toward a surgical site S and, upon movement of accessory support member 60, changes its position between first and second legs 14, 20 but remains directed toward surgical site S.

In heart surgery, the grippers 16 and 24, 26, are engaged with the tissue or ribs at the sides of an opening in the chest wall. By manual manipulation of handle 32, grippers 16 and 24, 26 are caused to move relatively away from each other to effectively expand and maintain the opening in the chest wall. The position of the TV camera or other accessory A may be changed by sliding support member 60 along rail 50 or by rotating the support member on the rail so as to tilt the camera or other accessory A to a desired angular position. If it is found helpful to further spread legs 14, 20, or to bring legs 14, 20 closer together, rail 50 is sufficiently flexible to bend with the leg movement. Moreover, by loosening lock screw 65 in sleeve 55, rail 50 may be shifted in sleeve 55 (to accommodate changes in the distance between legs 14 and 20) and then again fixed to prevent further movement by tightening down on lock screw 65.

Preferably accessory support member 60 is configured to make a tight sliding fit on rail 50, so that it can be slid manually along the rail but will retain its current position when released from the surgeon's hand. However it is more preferable to provide accessory support member 60 with a manually-operated lock screw 63 that can be turned into tight engagement with rail 50 so as to lock the accessory support member 60 in a selected position.

There is thus provided a retractor and an accessory device support assembly, wherein the retractor may be a selected one of number of currently available retractors, and wherein the accessory device support is easily moved so as to maintain an operative end of an accessory device directed at a surgical site.

It is to be understood that the present invention is by no means limited to the particular construction herein disclosed an/or shown in the drawings, but also comprises any modifications or equivalents within the scope of the claims. Thus, for example, accessory support member 60 could be fixed permanently in a selected positon on rail 50. Also, while the above description has focused on an assembly for use in heart surgery, and while it is contemplated that the assembly will find significant utility in that area, it will be apparent that the invention pertains equally and more generally to spreader tools in combination with support devices for a host of accessories, such as cameras, light sources, injection means, suction means, cutting means, and the like.

What is claimed is:

1. A surgical retractor assembly comprising:

an elongated base bar;

a first leg attached to and extending at a right angle to said base bar;

a first gripper disposed on said first leg;

a carriage mounted on and movable lengthwise of said base bar toward and away from said first leg;

a second leg having a proximal end thereof attached to said carriage, said second leg extending parallel to said first leg and at a right angle to said base bar, said second leg being movable with said carriage along said base bar;

a second gripper carried by said second leg;

a U-shaped flexible rail mounted adjacent its first and second opposite ends to said first and second legs respectively, with a bent portion of said rail extending proximate to said base bar; and an accessory support means mounted on said rail, said accessory support means being adapted to support an accessory device such that an operative portion of the accessory device is disposed between said first and second legs, whereby when said retractor is disposed in bone or tissue-retracting position relative to a surgical site, said operative portion of said accessory device is directed toward the surgical site.

2. An assembly according to claim 1 wherein said base bar is provided with a gear rack, and further including manually rotatatable gear means mounted to said carriage and coupled to said gear rack for causing said carriage to move along said base bar and thereby to move said second leg toward or away from said first leg.

3. An assembly according to claim 2 wherein said first leg is integral with said base bar.

4. An assembly according to claim 2 further including a handle member coupled to said gear means for rotating said gear means.

5. An assembly according to claim 1 wherein said first gripper comprises an elongated channel member mounted on said first arm.

6. An assembly according to claim 5 wherein said second gripper comprises at least one arm mounted on said second leg and extending toward said first leg, and curved fingers extending from a free end of said arm.

7. An assembly according to claim 1 further including an accessory device carried by said accessory support means.

8. An assembly according to claim 7 wherein said accessory device comprises a camera and the operative end of the accessory device comprises a lens portion of the camera.

9. An assembly according to claim 7 wherein the accessory device comprises a light source and the operative end of the accessory device comprises a light emitting portion of the light source.

10. A surgical spreader assembly assembly comprising:

an elongated base bar;

a first leg extending from said base bar and substantially normal thereto;

a first gripper disposed on said first leg;

a second leg mounted at a proximal end thereof on said base bar and extending parallel to said first leg, said second leg proximal end being movable along said base bar;

a second gripper disposed on said second leg;

a U-shaped flexible rail;

first means connecting a first end of said rail to said first leg and second means connecting a second end of said rail to said second leg, with a curved portion of said rail extending proximate said base bar; and an accessory support member mounted on said rail and slidably movable thereon, said accessory support member being adapted to retain an accessory device such that an operative end of the accessory device is disposed generally between said first and second legs.

11. An assembly according to claim 10 wherein said accessory device is a camera and said accessory support member is adapted to support the camera such that a lens portion of the camera is disposed generally between said first and second legs.

12. An assembly according to claim 10 wherein said accessory is a light source and said accessory support member is adapted to support the light source such that a light emitting portion of the light source is disposed generally between said first and second legs.

13. An assembly according to claim 10 further comprising means for locking said accessory support member in a selected location on said rail.

14. An assembly according to claim 10 further comprising means for locking said rail to said second means to fix said rail on said second leg, and for releasing said rail to permit movement of said rail relative to said second leg.

15. An assembly according to claim 14 wherein said second means comprises a sleeve fixed to said second leg and said means for locking and releasing said rail comprises a lock screw mounted in said sleeve and engageable with said rail.

16. A surgical spreader assembly assembly comprising:

an elongated base bar;

a first leg extending from said base bar and substantially normal thereto;

a first gripper disposed on said first leg;

a second leg mounted at a proximal end thereof on said base bar and extending parallel to said first leg, said second leg being movable relative to said base bar;

a second gripper disposed on said second leg;

a U-shaped flexible rail having a first end attached to said first leg and a second end attached to said second leg, with a curved portion of said rail extending proximate said base bar; and an accessory support member mounted on said rail and slidably movable thereon, said accessory support member being adapted to support an accessory device such that an operative end of the accessory device is disposed generally between said first and second legs.

17. An assembly according to claim 16 further comprising means for locking said accessory support member on said rail in a selected location.

* * * * *

UNITED STATES PATENT AND TRADEMARK OFFICE
CERTIFICATE OF CORRECTION

PATENT NO. : 5,697,891
DATED : December 16, 1997
INVENTOR(S) : Koichiro Hori

It is certified that error appears in the above-indentified patent and that said Letters Patent is hereby corrected as shown below:

Claim 10, column 5, line 12, delete the word "assembly" (second occurrence); and Claim 16, column 6, line 16, delete the word "assembly" (second occurrence).

Signed and Sealed this

Twenty-sixth Day of May, 1998

Attest:

BRUCE LEHMAN

Attesting Officer

Commissioner of Patents and Trademarks